United States Patent
Tanaka

(10) Patent No.: US 8,703,890 B2
(45) Date of Patent: Apr. 22, 2014

(54) POLYFUNCTIONAL POLYMER OF HIGH STEREOREGULARITY AND METHOD FOR PRODUCING THE SAME

(75) Inventor: Hitoshi Tanaka, Tokushima (JP)

(73) Assignee: The University of Tokushima, Tokushima-shi (JP)

( * ) Notice: Subject to any disclaimer, the term of this patent is extended or adjusted under 35 U.S.C. 154(b) by 73 days.

(21) Appl. No.: 13/138,210

(22) PCT Filed: Jan. 25, 2010

(86) PCT No.: PCT/JP2010/051301
§ 371 (c)(1),
(2), (4) Date: Jul. 20, 2011

(87) PCT Pub. No.: WO2010/084997
PCT Pub. Date: Jul. 29, 2010

(65) Prior Publication Data
US 2011/0282004 A1    Nov. 17, 2011

(30) Foreign Application Priority Data
Jan. 26, 2009   (JP) ................................ 2009-014816

(51) Int. Cl.
C08F 24/00   (2006.01)
C08F 34/02   (2006.01)
C07D 317/34  (2006.01)

(52) U.S. Cl.
USPC .......... 526/270; 525/55; 525/327.2; 525/360; 525/379; 525/383; 525/266; 549/296

(58) Field of Classification Search
USPC ......... 525/55, 327.2, 360, 379, 383; 526/266, 526/270; 549/296
See application file for complete search history.

(56) References Cited

U.S. PATENT DOCUMENTS

| | | |
|---|---|---|
| 5,498,799 A | 3/1996 | Torihara et al. |
| 2004/0248031 A1 | 12/2004 | Ansai et al. |

FOREIGN PATENT DOCUMENTS

| | | | |
|---|---|---|---|
| EP | 1447403 A1 | 8/2004 | |
| JP | 07-069960 | 3/1995 | |
| JP | 07-070106 | 3/1995 | |
| JP | 07069960 A | * 3/1995 | ............ C07C 49/433 |
| JP | 07070106 A | * 3/1995 | ............ C07D 317/34 |
| JP | 10-316609 A | 12/1998 | |
| JP | 2005-044710 | 2/2005 | |
| WO | WO-03/035637 | 5/2003 | |

OTHER PUBLICATIONS

Supplementary European Search Report dated Aug. 3, 2012 for European Patent Application No. 10733598.6.
Naohiro Hoshikawa et al., "Stereospecific Radical Polymerization of N-Triphenylmethylmethacrylamides Leading to Highly Isotactic Helical Polymers," J. Amer. Chem. Soc., 2003, vol. 125, No. 41, pp. 12380-12381.
Toyoharu Miyagawa et al., "A Novel Route to Poly($\alpha$-hydroxyacrylic acid) Derivatives by the Hydrolysis of Polymers Containing 1,3-Dioxolan-4—one Moiety," J. Polym. Sci.: Part A: Polym. Chem., 2001, vol. 39, pp. 1629-1633.
International Search Report dated May 11, 2010, issued for PCT/JP2010/051301.

* cited by examiner

*Primary Examiner* — Fred M Teskin
*Assistant Examiner* — Marie Reddick
(74) *Attorney, Agent, or Firm* — Edwards Wildman Palmer LLP

(57) ABSTRACT

This invention provides a polyfunctional polymer having high stereoregularity, in particular, isotacticity, and provides a production process thereof. The present invention relates to a polymer having, in a molecule, a repeating unit represented by General Formula (2):

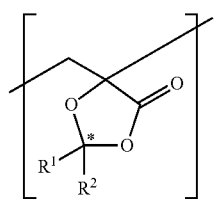

(2)

wherein $R^1$ and $R^2$ are different, and each represents a hydrogen atom, an alkyl group and an aryl group; * represents an asymmetrical carbon, the polymer containing meso diad (m) and racemo diad (r) at a proportion of 60:40 to 100:0 (m:r).

The invention also relates to chemical modifications and a production process of the polymer.

7 Claims, 6 Drawing Sheets

POLYFUNCTIONAL POLYMER OF HIGH STEREOREGULARITY AND METHOD FOR PRODUCING THE SAME

TECHNICAL FIELD

The present invention relates to a polyfunctional polymer having high stereoregularity, and a production process thereof.

BACKGROUND ART

Usually, it is difficult to obtain stereoregular polymers, in particular, isotactic polymers, by radical polymerization of vinyl monomers. So far, only several kinds of methacrylate and methacrylamide polymers having bulky ester substituents have been reported to have an isotactic structure (Non-Patent Document 1); however, the manufacture of these polymers is complicated. The polymers are unstable as they degrade with heat of several tens of degrees. Moreover, in the molecule these polymers have only one functional group, which is either an ester group or an amide group. As such, currently, it is difficult to produce polyfunctional polymers.

Non-Patent Document 2 discloses a production process of a bifunctional polymer having a hydroxy group and a carboxyl group in the monomer constituent unit. However, the bifunctional polymer obtained by this method does not have stereoregularity, in particular, high isotacticity. Moreover, in this bifunctional polymer, many intramolecular lactones derived from an atactic structure or syndiotactic structure are formed. Accordingly, this method is insufficient for production of a polyfunctional polymer in which the functionality of the hydroxy group and the carboxyl group are effectively exhibited.

Patent Document 1 reports production of a stereoregular polymer by living radical polymerization. However, this method produces N-isopropylacrylamide or like monofunctional polymers, and the method does not always ensure high isotacticity of the polymers.

CITATION LIST

Non-Patent Document

Non-Patent Document 1: Hoshikawa, N.; Hotta, Y.; Okamoto, Y. J., Amer. Chem. Soc. 2003, 125(41), 12380
Non-Patent Document 2: Miyagawa, T.; Sanda, F.; Endo, T. J., Polym. Sci. Part A: Polym. Chem. 2001, 39, 1629

SUMMARY OF INVENTION

Technical Problem

An object of the present invention is to provide a polyfunctional polymer having high stereoregularity, particularly to a polyfunctional polymer having isotacticity, and to provide a production process thereof.

Solution to Problem

The inventors of the present invention conducted extensive research to solve the above problems and discovered a novel method for producing a polymer having high stereoregularity (in particular, isotacticity), which is performed by radical polymerization using, as a raw material monomer, a 5-methylene-1,3-dioxolane-4-one derivative having an asymmetrical carbon in the 2-position, derived from L-lactic acid or ferment lactic acid. The inventors further found that hydrolysis of the resulting polymer converts the polymer into a polyfunctional polymer having a hydroxy group and a carboxyl group on the same carbon. The inventors conducted further research based on the findings and completed the present invention.

Specifically, the present invention provides a polyfunctional polymer and a production process thereof.

[Item 1]

A polymer having, in a molecule, a repeating unit represented by General Formula (2):

[Chem. 1]

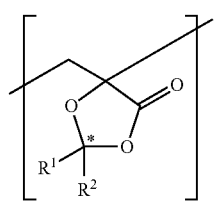

(2)

wherein $R^1$ and $R^2$ are different, and each represents a hydrogen atom, an alkyl group that may have a substituent, an aryl group that may have a substituent, or a heteroaryl group that may have a substituent; or $R^1$ and $R^2$ may be bonded to each other to form an asymmetric ring together with an adjacent asymmetrical carbon (C*); wherein * represents an asymmetrical carbon, the polymer containing meso diad (m) and racemo diad (r) at a proportion of 60:40 to 100:0 (m:r).

[Item 2]

A process for producing the polymer according to item 1, comprising subjecting a monomer containing a compound represented by General Formula (1):

[Chem. 2]

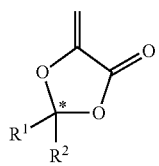

(1)

wherein $R^1$, $R^2$, and * are the same as above,
to radical polymerization.

[Item 3]

A process for producing a polymer having, in a molecule, a repeating unit represented by General Formula (3):

[Chem. 3]

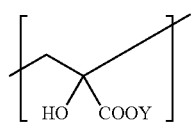

(3)

wherein, Y represents a hydrogen atom or countercation,
the polymer containing meso diad (m) and racemo diad (r) at a proportion of 60:40 to 100:0 (m:r), the process comprising subjecting a monomer containing a compound represented by General Formula (1) to radical polymerization to obtain the polymer according to item 1; and hydrolyzing the polymer,

[Chem. 4]

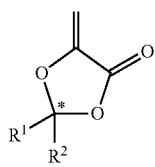

(1)

wherein $R^1$ and $R^2$ are different, and each represents a hydrogen atom, an alkyl group that may have a substituent, an aryl group that may have a substituent, or a heteroaryl group that may have a substituent; or $R^1$ and $R^2$ may be bonded to each other to form an asymmetric ring together with an adjacent asymmetrical carbon (C*); wherein * represents an asymmetrical carbon.

[Item 4]

A process for producing a polymer having, in a molecule, a repeating unit represented by General Formula (3):

[Chem. 5]

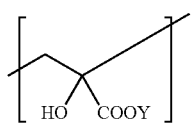

(3)

wherein, Y represents a hydrogen atom or countercation, the polymer containing meso diad (m) and racemo diad (r) at a proportion of 60:40 to 100:0 (m:r), the process comprising hydrolyzing the polymer according to item 1.

[Item 5]

A process for producing a polymer having, in a molecule, a repeating unit represented by General Formula (4):

[Chem. 6]

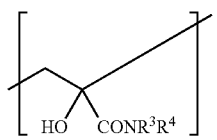

(4)

wherein, $R^3$ and $R^4$ are the same or different, and each represents a hydrogen atom, an alkyl group that may have a substituent, an aryl group that may have a substituent, or a heteroaryl group that may have a substituent; or $R^3$ and $R^4$ may be bonded to each other to form a ring together with an adjacent nitrogen (N), the polymer containing meso diad (m) and racemo diad (r) at a proportion of 60:40 to 100:0 (m:r), the process comprising reacting the polymer according to item 1 with a compound represented by General Formula (5):

$$HNR^3R^4 \qquad (5)$$

wherein $R^3$ and $R^4$ are the same as above.

[Item 6]

A process for producing a polymer having, in a molecule, a repeating unit represented by General Formula (6):

[Chem. 7]

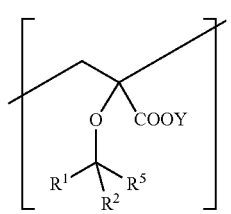

(6)

wherein, $R^1$ and $R^2$ are different, and each represents a hydrogen atom, an alkyl group that may have a substituent, an aryl group that may have a substituent, or a heteroaryl group that may have a substituent; or $R^1$ and $R^2$ may be bonded to each other to form an asymmetric ring together with an adjacent carbon; $R^5$ represents an alkyl group that may have a substituent, an aryl group that may have a substituent, or a heteroaryl group that may have a substituent, and Y represents a hydrogen atom or countercation, the polymer containing meso diad (m) and racemo diad (r) at a proportion of 60:40 to 100:0 (m:r), the process comprising reacting the polymer according to item 1 with a compound represented by General Formula (7):

$$R^5\text{-M} \qquad (7)$$

wherein M represents a metal atom, and $R^5$ is the same as above.

[Item 7]

A process for producing a polymer having, in a molecule, a repeating unit represented by General Formula (8):

[Chem. 8]

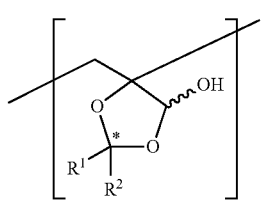

(8)

wherein $R^1$ and $R^2$ are different, and each represents a hydrogen atom, an alkyl group that may have a substituent, an aryl group that may have a substituent, or a heteroaryl group that may have a substituent; or $R^1$ and $R^2$ may be bonded to each other to form an asymmetric ring together with an adjacent asymmetrical carbon (C*); wherein * represents an asymmetrical carbon, the polymer containing meso diad (m) and racemo diad (r) at a proportion of 60:40 to 100:0 (m:r), the process comprising reducing the polymer according to item 1.

[Item 8]
A compound represented by General Formula (1c):

[Chem. 9]

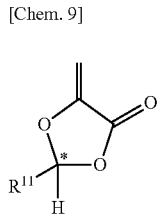

(1c)

wherein $R^{11}$ represents an ethyl group, a n-propyl group or an isopropyl group, and * represents an asymmetrical carbon.

Advantageous Effects of Invention

The production process of the present invention produces a polyfunctional polymer having high stereoregularity, in particular, isotacticity. Moreover, the production process also produces a polymer with a controlled molecular weight and molecular weight distribution. Further, since the resulting polymer is polyfunctional, it can be converted into a diverse polymer through chemical conversion.

DESCRIPTION OF EMBODIMENTS

Figure 1:
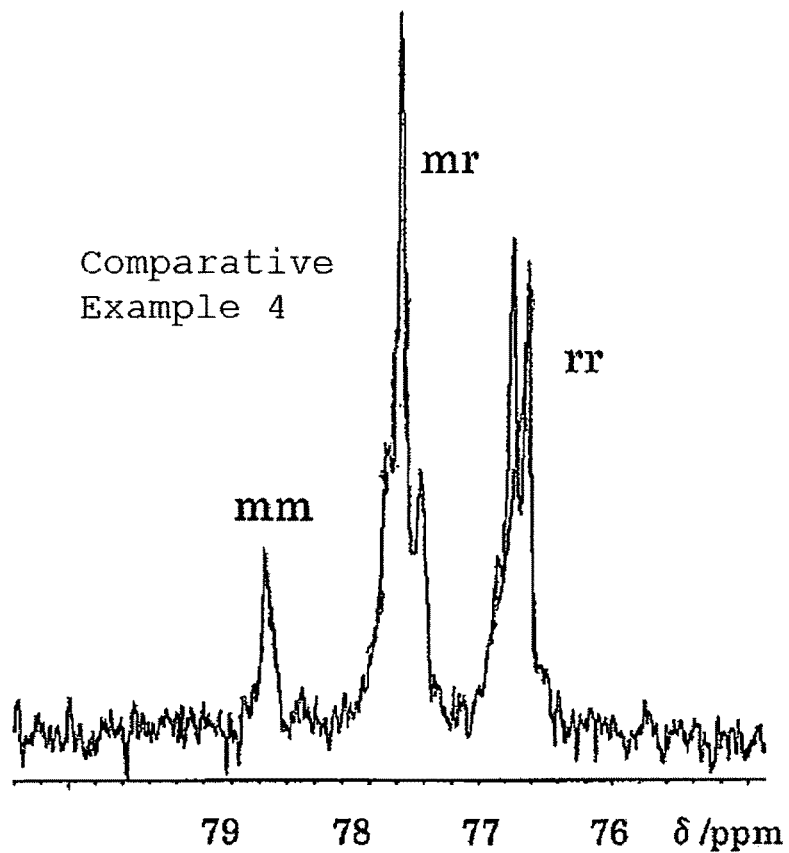
FIG. 1 shows $^{13}$C-NMR charts regarding main chain quaternary carbon regions of polymers obtained in Comparative Example 4 and Example 8.
Figure 1:
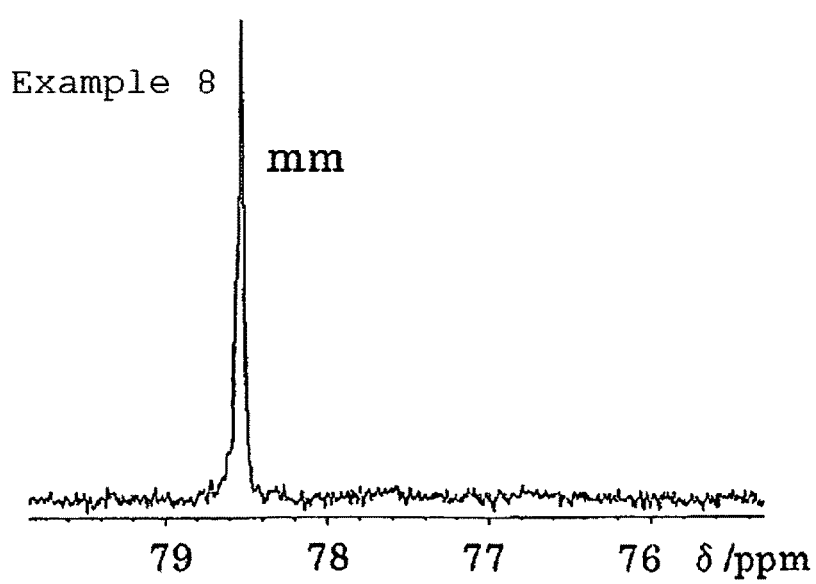

The present invention is more specifically described below.
1. Polymer Production The polymer of the present invention includes the polymer obtained by subjecting a monomer containing the compound represented by General Formula (1) to a radical polymerization reaction, and having a repeating unit represented by General Formula (2) in the molecule; and polymers obtained by chemically converting said polymer, which are polymers having repeating units represented by General Formulas (3), (4), (6), and (8).

The following separately explains a step of producing a polymer by subjecting a monomer to a radical polymerization reaction and a step of chemically converting (modifying) the obtained polymer.
1.1 Radical Polymerization Reaction The polymer having a repeating unit represented by General Formula (2) is produced, for example, by reacting the compound represented by General Formula (1) with another radical reactive monomer as required. A specific production scheme is shown below.

[Chem. 10]

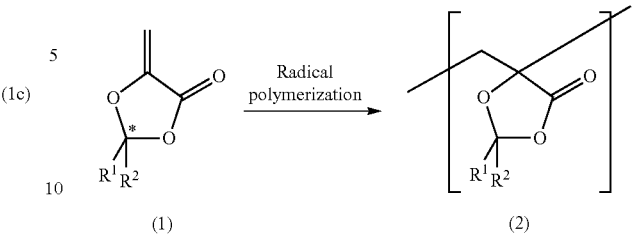

wherein, $R^1$ and $R^2$ are different, and each represents a hydrogen atom, an alkyl group that may have a substituent, an aryl group that may have a substituent, or a heteroaryl group that may have a substituent; or $R^1$ and $R^2$ may be bonded to each other to form an asymmetric ring together with an adjacent asymmetrical carbon (C*). "*" represents an asymmetrical carbon.

Examples of the alkyl group represented by $R^1$ or $R^2$ that may have a substituent include linear, branched, or cyclic alkyl groups having 1 to 10 carbon atoms. Specifically, examples thereof include alkyl groups having 1 to 6 carbon atoms, such as methyl, ethyl, n-propyl, isopropyl, n-butyl, isobutyl, sec-butyl, tert-butyl, pentyl, cyclopentyl, hexyl, cyclohexyl, or isohexyl. Among these, ethyl and isopropyl are preferable, and isopropyl is particularly preferable. The alkyl group may contain, for example, 1 to 3 substituents, such as a halogen atom (for example, fluorine, chlorine, or bromine), a carboxyl group, an ester group, an amide group, or a protected or unprotected hydroxy group.

Examples of the aryl group represented by $R^1$ or $R^2$ that may have a substituent include monocyclic or polycyclic aryl groups. Specific examples thereof include phenyl, toluoyl, xylyl, naphthyl, anthryl, and phenanthryl. The aryl group may contain, for example, 1 to 3 substituents, such as an alkyl group (for example, C1-6 alkyl group), a halogen atom (for example, fluorine, chlorine, or bromine), a carboxyl group, an ester group, an amide group, or a protected or unprotected hydroxy group.

Examples of the heteroaryl group represented by $R^1$ or $R^2$ that may have a substituent include heteroaryl groups containing oxygen, nitrogen, and/or a sulfur atom in the ring. Specific examples thereof include furyl, thienyl, imidazolyl, pyrazolyl, isoxazolyl, pyridyl pyrazinyl, pyrimidinyl, pyridazinyl, indolyl, quinolyl, isoquinolyl, and thiazolyl. The heteroaryl group may contain, for example, 1 to 3 substituents, such as an alkyl group (for example, C1-6 alkyl group), a halogen atom (for example, fluorine, chlorine, or bromine), a carboxyl group, an ester group, an amide group, or a protected or unprotected hydroxy group.

$R^1$ and $R^2$ may be bonded to each other to form an asymmetric ring together with an adjacent asymmetrical carbon (C*). For example, $R^1$ and $R^2$ may form a 3- to 8-membered cyclic hydrocarbon wherein the cyclic hydrocarbon contains, for example, in an asymmetric manner, 1 to 4 substituents, such as alkyl group (for example, C1-6 alkyl group), a halogen atom (for example, fluorine, chlorine, or bromine), a carboxyl group, an ester group, an amide group, or a protected or unprotected hydroxy group.

Since $R^1$ and $R^2$ are different, the carbon atom to which $R^1$ and $R^2$ are bonded is an asymmetrical carbon (C*). In the compound represented by General Formula (1) used in the present invention, R-isomer and S-isomer, which describe the steric structure in the asymmetrical carbon, have the following molar ratio: R-isomer (S-isomer):S-isomer (R-isomer)=70:30 to 100:0, preferably 75:25 to 100:0, more preferably 80:20 to 100:0.

A particularly preferable monomer represented by General Formula (1) is, in view of the stereoregularity of the polymer after the radical polymerization, a compound represented by General Formula (1c).

[Chem. 11]

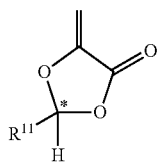

(1c)

wherein, $R^{11}$ represents an ethyl group, a n-propyl group or an isopropyl group, and * represents an asymmetrical carbon.

$R^{11}$ is preferably an isopropyl. The asymmetrical carbon (C*) may have the above steric structure with the above molar ratio specified as R-isomer (S-isomer):S-isomer (R-isomer).

A specific production process of the polymer having a repeating unit represented by General Formula (2) is described below.

The polymer having a repeating unit represented by General Formula (2) is produced by subjecting the monomer represented by General Formula (1) to radical polymerization. In a usual process, the monomer represented by General Formula (1) is mixed with a radical polymerization initiator as required in a container in which an inactive gas was substituted or in a vacuum-deaerated container, and the mixture is stirred.

The radical polymerization reaction may be performed without a solvent or with a solvent (organic solvent or aqueous solvent) generally used for radical polymerization. Examples of the organic solvents include benzene, toluene, N,N-dimethylformamide (DMF), dimethylsulfoxide (DMSO), acetone, chloroform, carbon tetrachloride, tetrahydrofuran (THF), ethyl acetate, chlorobenzene, dichlorobenzene, trifluoro methyl benzene, and anisole. Examples of aqueous solvents include water and those containing water and, as required, methanol, ethanol, isopropanol, n-butanol, ethyl cellosolve, butyrocellosolve, 1-methoxy-2-propanol, or the like.

When a solvent is used, the amount thereof is suitably adjusted; for example, the amount is 0.1 to 20 L, preferably 0.2 to 5 L, in general, based on 1 mol of the monomer represented by General Formula (1), or for copolymerization, based on 1 mol of all the monomers including the monomer represented by General Formula (1).

The radical polymerization reaction may be performed in the presence or absence of a radical polymerization initiator. Generally, it is preferable to perform the radical polymerization reaction in the presence of a radical polymerization initiator. It is, however, of course possible to perform spontaneous thermal polymerization in the absence of a radical polymerization initiator or to perform radical polymerization by photo irradiation in the presence or absence of a radical polymerization initiator. When performing radical polymerization using photo irradiation, a light source, such as a mercury lamp or a xenon lamp, is generally used for polymerization. A suitable light source may be selected according to the type of the vinyl monomer, the type of the polymerization initiator, etc.

The radical polymerization reaction also includes radical copolymerization, in addition to the radical homopolymerization of the monomer represented by General Formula (1). When performing radical copolymerization, in particular, when performing living radical copolymerization, it is possible to perform diblock and triblock copolymerizations. The monomers usable for radical copolymerization are not limited and include various monomers represented by General Formula (1) and any other monomers usable for radical polymerization.

Examples of the monomers usable for radical polymerization other than the monomers represented by General Formula (1) (hereinafter referred to as "comonomer") include (meth)acrylic esters, such as methyl (meth)acrylate, ethyl (meth)acrylate, (meth)acrylic acid, 2-hydroxyethyl (meth)acrylate, or menthyl(meth)acrylate; captodative substituted monomers (monomers in which the α-position is substituted simultaneously with an electron-donating group and an electron-accepting group), such as α-acetoxyacrylic acid, methyl α-acetoxyacrylate, menthyl α-acetoxyacrylate, α-acetoamidacrylic acid, methyl α-acetamidoacrylate, menthyl α-acetamidoacrylate, methyl α-methoxyacrylate, or menthyl α-methoxyacrylate; unsaturated monomers containing cycloalkyl groups (cycloalkyl-group-containing (meth)acrylate), such as cyclohexyl (meth)acrylate, isobornyl (meth)acrylate, or adamantyl (meth)acrylate; unsaturated monomers containing two or more carboxyl groups, such as maleic acid, fumaric acid, dimethyl fumarate, dibutyl fumarate, itaconic acid, ethyl itaconate, maleic anhydride, maleimide, N-cyclohexyl maleimide, or N-phenyl maleimide; amine-containing unsaturated monomers (amide(meth)acrylate), such as (meth)acrylamide, N,N-dimethyl(meth)acrylamide, or N-hydroxyethyl(meth)acrylamide; aromatic unsaturated monomers, such as styrene, α-methylstyrene, α-methoxystyrene, α-methoxy-2-methoxystyrene, 2-methylstyrene, 4-methylstyrene, 4-tert-butoxystyrene, 4-chlorostyrene, 2,4-dichlorostyrene, 1-vinylnaphthalene, divinylbenzene, 4-styrenesulfonic acid, or alkali metal salts thereof (e.g., sodium salts or potassium salts); hetero-ring-containing unsaturated monomers, such as 2-vinylpyridine, 4-vinylpyridine, 2-vinylthiophene, 1-vinyl-2-pyrrolidone, or vinylcarbazole; vinylamides, such as N-vinylacetamide or N-vinylbenzoylamide; α-olefins, such as ethylene, propylene, or 1-hexene; diene monomers, such as butadiene or isoprene; polyfunctional monomers, such as divinylbenzene or 4,4'-divinylbiphenyl; (meth)acrylonitrile, methyl vinylketone, methyl isopropenyl ketone, ethyl vinylsulfide, vinyl benzonate, vinyl acetate, vinyl chloride, vinylidene chloride, ethyl α-cyanoacrylate, coumarin, indene, or indone.

In the present invention, when a comonomer is used in addition to the monomer represented by General Formula (1), the amount of the comonomer in the entire monomer amount is generally not more than 40 mol %, preferably not more than 30 mol %, more preferably not more than 20 mol %. Further, for the polymer having a repeating unit represented by General Formula (2) obtained by a radical polymerization reaction, the mole fraction derived from the comonomer is generally not more than 20 mol %, preferably not more than 15 mol %, more preferably not more than 12 mol %.

The radical polymerization initiator may be any general initiator useful for radical polymerization. Examples thereof include azo polymerization initiators; peroxides such as benzoyl peroxide, t-butylhydro peroxide, or cumene hydroperoxide; redox polymerization initiators; and photopolymerization initiators, such as 2,2-dimethoxy-1,2-diphenylethane-1-one or bis(2,4,6-trimethylbenzoyl)-phenylphosphine oxide. Further, in addition to the above initiators, living radical polymerization initiators using organic halogen substances (for example, ethyl 2-bromo isobutylate), nitroxide derivatives, thiocarbonyl substances, organotellurium substances, or the like, as the initiator or an additive.

Among the above polymerization initiators, azo polymerization initiators are preferable. Specific examples thereof include 2,2'-azobis(isobutyronitrile)(AIBN), 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(cyclohexane-1-carbonitrile), 2,2'-azobis(2-methylpropane), 2,2'-azobis(2,4,4-trimethylpentane), and 2,2'-azobis[2-(3,4,5,6-tetrahydropyrimidine-2-yl)propane]dihydro chloride.

The amount of the radical polymerization initiator can be suitably adjusted depending on the polymer to be obtained. Generally, the amount of the radical polymerization initiator is $1 \times 10^{-6}$ to 1 mol, preferably $1 \times 10^{-4}$ to $1 \times 10^{-1}$, more preferably $1 \times 10^{-3}$ to $1 \times 10^{-2}$, based on 1 mol of the monomer represented by General Formula (1), or for copolymerization, based on 1 mol of all the monomers including the monomer represented by General Formula (1).

Among the above radical polymerization methods, living radical polymerization is particularly preferable, because it produces a polymer with even higher control of molecular weight, molecular weight distribution, steric structure, etc.

Preferable examples of living radical polymerization initiators include organotellurium-mediated living radical polymerization initiators, such as AIBN/di-n-butyl ditelluride (DBT), AIBN/diphenylditelluride, AIBN/ethyl-2-methyl-2-methyltellanyl-propionate, AIBN/ethyl-2-methyl-2-butyltellanyl-propionate (EMBTP), AIBN/ethyl-2-methyl-2-phenyltellanyl-propionate, and AIBN/DBT/EMBTP.

The amount of AIBN is suitably adjusted depending on the polymer to be obtained. Generally, the amount of AIBN is $1 \times 10^{-6}$ to 1 mol, preferably $1 \times 10^{-4}$ to $1 \times 10^{-1}$, more preferably $1 \times 10^{-3}$ to $1 \times 10^{-2}$, based on 1 mol of the monomer represented by General Formula (1), or for copolymerization, based on 1 mol of all the monomers including the monomer represented by General Formula (1). The amount of organotellurium is generally $1 \times 10^{-6}$ to 1 mol, preferably $1 \times 10^{-4}$ to $1 \times 10^{-1}$, more preferably $1 \times 10^{-3}$ to $1 \times 10^{-2}$, based on 1 mol of the monomer represented by General Formula (1), or for copolymerization, based on 1 mol of all the monomers including the monomer represented by General Formula (1).

Among living radical polymerization methods, in particular, the block copolymer is produced as follows. This copolymerization is performed using at least one monomer represented by General Formula (1) and may also use the aforementioned comonomers. For AB-type diblock copolymerization, for example, the monomer represented by General Formula (1) is reacted in a nitrogen-substituted glove box or in a deaerated container in the presence or absence of a solvent using the above radical initiator, thereby obtaining the polymer having a repeating unit represented by General Formula (2). Thereafter, the second monomer (a different kind of monomer represented by General Formula (1) or a comonomer) is added to obtain a copolymer. Further, it is also possible to add the monomers in reverse order, i.e., the second monomer is reacted first, and then the monomer represented by General Formula (1) is reacted. ABA-type, ABC-type, or other triblock copolymers may also be produced by sequentially adding monomers after the production of a diblock copolymer.

The reaction temperature and the reaction time may be adjusted according to the type of the vinyl monomer and the type of the polymerization initiator. Generally, the reaction is carried out by stirring for 0.5 to 100 hours at about 0 to 180° C., preferably for 1 to 30 hours at 30 to 100° C. The reaction is generally carried out under normal pressure; however, it may also be performed under elevated or reduced pressure.

The inactive gas used herein may be nitrogen, argon, helium, or the like. Argon and nitrogen are preferable. Nitrogen is particularly preferable.

The polymerization reaction produces a stereoregular polymer that comprises a repeating unit represented by General Formula (2). The ratio of meso diad (m) to racemo diad (r) in this polymer (m:r) is 60:40 to 100:0. The ratio (m:r) is preferably 65:35 to 100:0, more preferably 70:30 to 100:0, further preferably 75:25 to 100:0, and particularly preferably 80:20 to 100:0. The ratio is confirmed through $^{13}$C-NMR analysis of the polymer having a repeating unit represented by General Formula (3), which is obtained by the later-described ring-opening reaction.

In the polymer having a repeating unit represented by General Formula (2), generally, the solubility with respect to organic solvents (for example, benzene, and toluene) decreases as the proportion of m(meso) increases.

Although the polymerization degree of the polymer obtained by the radical polymerization reaction of the present invention may be suitably adjusted depending on the reaction time, concentration of the initiator, reaction temperature, solvent, etc., the number-average degree of polymerization of the polymer is 10 to 20,000, particularly 50 to 5,000. The number-average molecular weight (Mn) is about 1,000 to 4,000,000, preferably about 5,000 to 1,000,000. The measurements of Mn and weight-average molecular weight (Mw) are performed using the GPC method that is used in the Examples. The present invention generally produces a radical polymer having a molecular weight distribution (PDI=Mw/Mn) of 1.01 to 4.0, particularly 1.05 to 2.5. The molecular weight distribution (PDI=Mw/Mn) of the living radical polymer is particularly narrow, i.e., it is specified between 1.01 to 1.5, or can be further specified to 1.05 to 1.30, or 1.1 to 1.25.

1.2 Chemical Conversion (Modification) of Polymer

The polymer obtained by the radical polymerization reaction as described in the above section 1.1 may be chemically converted (modified) through a ring-opening reaction (hydrolysis, nucleophilic substitution reaction, etc.), reduction reaction, and the like. Through chemical conversion, the polymer is converted into a polymer in which the main chain keeps high stereoregularity and has various functional groups or properties. A specific production scheme is shown below.

[Chem. 12]

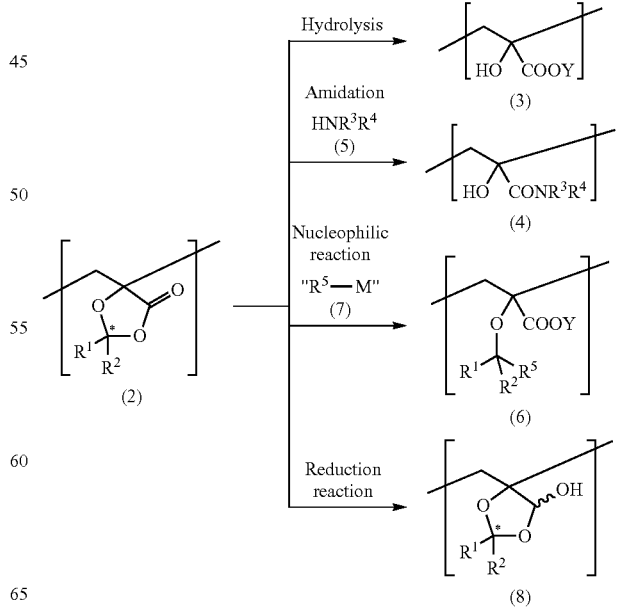

wherein, $R^3$ and $R^4$ are the same or different, and each represents a hydrogen atom, an alkyl group that may have a substituent, an aryl group that may have a substituent, or a heteroaryl group that may have a substituent; or $R^3$ and $R^4$ may be bonded to each other to form a ring together with an adjacent nitrogen (N). Y represents a hydrogen atom or a countercation. $R^5$ represents an alkyl group that may have a substituent, an aryl group that may have a substituent, or a heteroaryl group that may have a substituent. M represents a metal atom.

Hydrolysis

Each obtained polymer having a repeating unit represented by General Formula (2) has a 1,3-dioxolan-4-one skeleton, which is then converted into a hydroxycarboxylic acid through hydrolysis reaction. As required, the carboxylic acid can be converted into a carboxylate.

Examples of the countercation represented by Y include metallic cations, ammonium, and onia of nitrogen-containing organic compounds. Examples of metallic cations include alkali metal ions, such as sodium ions or potassium ions; and alkali earth metal ions, such as calcium, barium, or magnesium. Examples of the onia of nitrogen-containing organic compounds include (mono-, di-, tri-, or tetra-) alkyl ammonium, pyridinium, piperidinium, quinolinium, and thiophenium.

The polymer having a repeating unit represented by General Formula (2) is dissolved in water and an organic solvent (an ether solvent, such as THF, or a halogenated hydrocarbon solvent, such as chloroform), or is swollen by being wet with water and the organic solvent, and then hydrolysis is performed by adding a base or an acid. After the reaction, the solvent is distilled off from the reaction mixture, and a poor solvent (for example, methanol) is added to the residue to precipitate a polymer, thereby obtaining a hydrolysate. When a part of the filtered hydrolyzed polymer is water-insoluble, the filtrate is mixed with water, and only a portion dissolved in water is obtained as a hydrolysate. Further, after the reaction, as required, the carboxylate may be converted into a carboxylic acid using an acid (for example, hydrochloric acid).

Examples of the hydrolysis reagent include, as an acid, hydrochloric acid, sulfuric acid, trifluoro sulfuric acid, trichloro acetic acid, trifluoro acetic acid, and paratoluene sulfonic acid. Examples of the bases include hydroxides of alkali metal, such as NaOH or KOH; hydroxides of alkali earth metal, such as $Be(OH)_2$ or $Mg(OH)_2$; acids, such as sulfuric acid, nitric acid, LiCl, $BF_3$, or $SnCl_4$; and metal alkoxides, such as $CH_3ONa$ or $(CH_3)_3OK$. The bases and the acids may be used in the form of aqueous solutions as required.

The reaction conditions for hydrolysis may be determined in reference to known methods. For example, about 1 to 50 g of a base is used per gram of the polymer having a repeating unit represented by General Formula (2), and the mixture is reacted in a solvent (for example, water, ether solvent, or halogenated hydrocarbon solvent) for about 1 to 100 hours at 0 to 150° C. The reaction conditions for hydrolysis may be determined in reference to known methods.

Instead of such a chemical hydrolysis reagent, enzymatic hydrolysis may also be performed. Examples of hydrolytic enzymes include lipase, protease, phosphoesterase, esterase, cutinase, and combination of these enzymes. The reaction conditions for enzymatic hydrolysis may be determined in reference to known methods.

Amidation (Aminolysis)

Each obtained polymer having a repeating unit represented by General Formula (2) has a 1,3-dioxolan-4-one skeleton and may be amidated by reacting the amine represented by the following general formula: $HN R^3, R^4$ (5) (wherein, $R^3$ and $R^4$ are the same as above) with the carbonyl carbon of lactone.

Examples of the alkyl group represented by $R^3$ or $R^4$ that may have a substituent include linear, branched, or cyclic C1-10 alkyl groups. Specific examples thereof include C1-6 alkyl groups, such as methyl, ethyl, n-propyl, isopropyl, n-butyl, isobutyl, sec-butyl, tert-butyl, pentyl, cyclopentyl, hexyl, cyclohexyl, or isohexyl. Ethyl or isopropyl is preferable, and isopropyl is particularly preferable. The alkyl group may have 1 to 3 substituents, such as a halogen atom (for example, fluorine, chlorine, or bromine), a carboxyl group, an ester group, an amide group, a protected or unprotected hydroxy group, or the like.

Examples of the aryl group represented by $R^3$ or $R^4$ that may have a substituent include monocyclic or polycyclic aryl groups. Examples thereof include phenyl, toluoyl, xylyl, naphthyl, anthryl, and phenanthryl. The aryl group may contain 1 to 3 substituents, such as an alkyl group (for example, C1-6 alkyl group), a halogen atom (for example, fluorine, chlorine, or bromine), a carboxyl group, an ester group, an amide group, or a protected or unprotected hydroxy group.

Examples of the heteroaryl group represented by $R^3$ or $R^4$ that may have a substituent include heteroaryl groups containing oxygen, nitrogen, and/or sulfur atom in the ring, such as furyl, thienyl, imidazolyl, pyrazolyl, isoxazolyl, pyridyl, pyrazinyl, pyrimidinyl, pyridazinyl, indolyl, quinolyl, isoquinolyl, and thiazolyl. The heteroaryl group may contain 1 to 3 substituents, such as an alkyl group (for example, C1-6 alkyl group), a halogen atom (for example, fluorine, chlorine, or bromine), a carboxyl group, an ester group, an amide group, or a protected or unprotected hydroxy group.

$R^3$ and $R^4$ may be bonded to each other to form a ring together with an adjacent nitrogen atom (N). For example, they may form a 3- to 8-membered nitrogen-containing cyclic hydrocarbon (for example, aziridine, azetidine, pyrrolidine, or piperidine), wherein the nitrogen-containing cyclic hydrocarbon may have 1 to 4 substituents, such as an alkyl group (for example, C1-6 alkyl group), a halogen atom (for example, fluorine, chlorine, or bromine), a carboxyl group, ester group, amide group, or a protected or unprotected hydroxy group.

The amidation may be performed using a compound (amine or ammonia) represented by General Formula (5) or an aluminum reagent represented by General Formula (5').

$$LiAl(NR^3R^4)_4 \qquad (5')$$

The aluminium reagent represented by General Formula (5') may be prepared from the compound represented by General Formula (5), according to the disclosure of Ashby, E. C.; Beach, R. G., Inorg. Chem. 1971, 10, 1888.

Further, the reaction between the polymer having a repeating unit represented by General Formula (2) and the compound represented by General Formula (5) or (5') is performed, for example, using about 1 to 50 g of the reagent represented by General Formula (5) or (5') per gram of the polymer having a repeating unit represented by General Formula (2) in a solvent (for example, ether solvent, or halogenated hydrocarbon solvent) for about 0.5 to 20 hours at −30 to 80° C. The reaction conditions for hydrolysis may be determined in reference to known methods.

Reduction Reaction

Each obtained polymer having a repeating unit represented by General Formula (2) has a 1,3-dioxolan-4-one skeleton, which can be converted into a 1,3-dioxolan-4-ol through a reduction reaction.

Examples of reduction reagents used for the reduction reaction include Clemmensen reduction reagents, such as Zn(Hg), and Wolff-Kishner reduction reagents, such as H$_2$NNH$_2$(KOH), LiAlH$_4$, LiAlH(OC$_2$H$_5$)$_3$, LiAlH(O-tert-C$_4$H$_9$)$_3$, AlH (iso-C$_4$H$_9$)$_3$, NaAlH$_2$(OCH$_2$CH$_2$OCH$_3$)$_2$, LiBH$_4$, LiBH(C$_2$H$_5$)$_3$, NaBH$_4$, (C$_2$H$_5$)$_3$SiH, (n-C$_3$H$_7$)$_3$SiH, and Cl$_3$SiH. The reaction conditions for reduction may be determined in reference to known methods.

Nucleophilic Reaction

When performing a ring-opening reaction by a nucleophilic reaction of a carbon hydride group, the compound having a bond represented by General Formula (7) (organic metal reagent) is used.

$$R^5\text{-M} \quad (7)$$

wherein, M represents a metal atom, in particular, Mg, Li, or Cu.

Examples of the organic metal reagent include organic lithium (R$^5$Li) or Grignard reagents (R$^5$MgZ; Z represents a halogen atom, such as chlorine, bromine, or iodine) and mixture catalysts containing those reagents and a copper halide, such as CuCl or CuBr.

Examples of the alkyl group represented by R$^5$ that may have a substituent include linear, branched, or cyclic C1-10 alkyl groups. Specific examples thereof include C1-6 alkyl groups, such as methyl, ethyl, n-propyl, isopropyl, n-butyl, isobutyl, sec-butyl, tert-butyl, pentyl, cyclopentyl, hexyl, cyclohexyl, or isohexyl. Ethyl or isopropyl is preferable, and isopropyl is particularly preferable. The alkyl group may have 1 to 3 substituents, such as a protected or unprotected hydroxy group or a phenyl group.

Examples of the aryl group represented by R$^5$ that may have a substituent include monocyclic or polycyclic aryl groups. Examples thereof include phenyl, toluoyl, xylyl, naphthyl, anthryl, and phenanthryl. The aryl group may contain 1 to 3 substituents, such as an alkyl group (for example, C1-6 alkyl group) or a protected or unprotected hydroxy group.

Examples of the heteroaryl group represented by R$^5$ that may have a substituent include heteroaryl groups containing oxygen, nitrogen, and/or sulfur atom in the ring, such as furyl, thienyl, imidazolyl, pyrazolyl, isoxazolyl, pyridyl, pyrazinyl, pyrimidinyl, pyridazinyl, indolyl, quinolyl, isoquinolyl, or thiazolyl. The heteroaryl group may contain 1 to 3 substituents, such as an alkyl group (for example, C1-6 alkyl group), or a protected or unprotected hydroxy group.

The nucleophilic reaction may be performed using the compound having a bond represented by General Formula (7) (organic metal reagent) according to a known method. For example, the organic metal reagent and the polymer having a repeating unit represented by General Formula (2) are reacted.

With these methods, the polymers having repeating units represented by General Formulas (3), (4), (6), and (8) are produced. The resulting polymers retain the same ratio (m:r) of meso diad (m) and racemo diad (r), polymerization degree, molecular weight distribution, etc., as the polymer having a repeating unit represented by General Formula (2).

2. Raw Material Monomer Production

The monomer represented by Formula (1) is produced in various ways. For example, the monomer may be produced according to the disclosure of MaGee, D. I., et al., Tetrahedron, 62, 4153-61 (2006). A specific production scheme is shown below.

[Chem. 13]

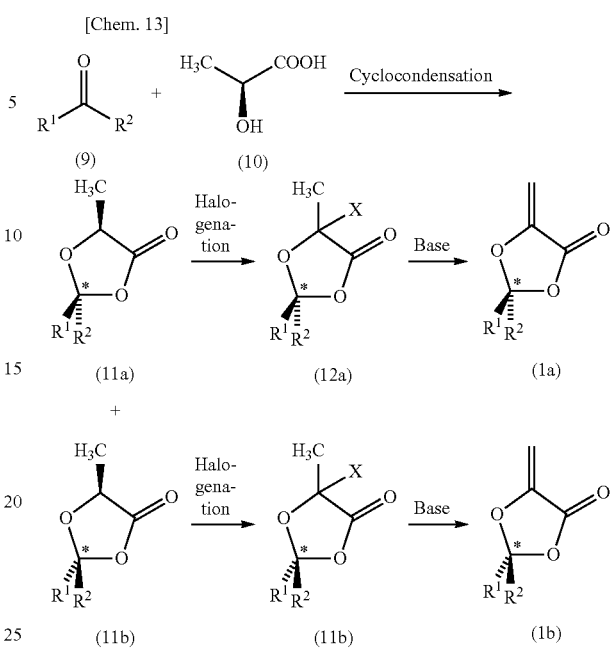

wherein, X represents a halogen atom, and R$^1$, R$^2$ and * are the same as above.

Examples of lactic acid represented by General Formula (10) include L-lactic acid, D-lactic acid, and ferment lactic acid. Although the above scheme uses L-lactic acid for the sake of convenience, the production may also be performed using its enantiomer, i.e., D-lactic acid. In this case, the compound in the scheme has an inverse steric configuration of the asymmetrical carbon. Further, ferment lactic acid may be used as a material (green chemistry). In particular, since the ferment lactic acid contains a sufficient amount of L-lactic acid, the process for separating the enantiomer can be omitted. More specifically, the polymer obtained by radical polymerization of a monomer derived from ferment lactic acid has sufficiently high stereoregularity (isotacticity). This is very important in terms of industrial manufacture.

The carbonyl compound represented by General Formula (9) (for example, isobutylaldehyde) and L-lactic acid represented by General Formula (10) are refluxed in a solvent (for example, carbon hydride solvent, such as n-pentane) in the presence of an acid catalyst (for example, p-toluene sulfonic acid, methane sulfonic acid, or sulfuric acid) while azeotropically removing water using a reflux condenser attached to a Dean-Stark fractionator.

A variety of known aldehydes and ketones may be used as the carbonyl compound represented by General Formula (9). Examples of aldehydes include acetoaldehyde, propionaldehyde, n-butylaldehyde, isobutyl aldehyde, pivalaldehyde, valeraldehyde, trifluoroethanal, chloral, succin aldehyde, chlorofluoro acetoaldehyde, menthone, cyclohexane carbaldehyde, 2-pyrrole carbaldehyde, 3-pyridine carbaldehyde, 2-furaldehyde, benzaldehyde, benzene acetoaldehyde, vanillin, piperonal, and citronellal. Examples of ketones include methyl ethyl ketone, 2-pentanone, 2-hexanone, methyl sec-butyl ketone, methyl tert-butyl ketone, acetophenone, 2-furyl methyl ketone, 2-acetonaphthone, 2(3H)-pyrazinone, and pyrrolidone. Among these, acetoaldehyde, propionaldehyde, n-butyl aldehyde, isobutyl aldehyde, and pivalaldehyde are preferable. Isobutyl aldehyde is more preferable.

The condensation reaction generally produces a mixture of two diastereomers represented by General Formulas (11a) and/or (11b). They may be separated and purified, for example, by distillation under a normal or reduced pressure or by column chromatography. When a mixture of the compounds represented by General Formulas (11a) and (11b) is obtained, the above methods for separation and purification may be used.

The temperature and time of a condensation reaction may be suitably adjusted, for example, according to the type of reagent. The reaction temperature is generally set to about 0 to 180° C., preferably 0 to 80° C., more preferably 0 to 60° C. Further, the reaction time is generally 0.5 to 100 hours, preferably 0.5 to 30 hours, more preferably 0.5 to 10 hours. The temperature and time conditions of a condensation reaction greatly affect the generation ratio of (11a) and (11b); generally, reaction at a low temperature for a short time increases the generation ratio. In particular, by carrying out the reaction for 0.5 to 10 hours at 0 to 60° C., a high diastereomeric ratio can be achieved.

When the compound represented by General Formula (11a) and the compound represented by General Formula (11b) are mixtures, it is preferable to contain one of the compounds at high purity (at a high diastereomeric ratio) in view of increasing stereoregularity of the polymer resulting from the polymerization. For example, the molar ratio of the compound represented by General Formula (11a) to the compound represented by General Formula (11b) is 70:30 to 100:0, preferably 80:20 to 100:0, more preferably 90:10 to 100:0, particularly preferably 95:5 to 100:0, and the molar ratio of the compound represented by General Formula (11b) to the compound represented by General Formula (11a) is 70:30 to 100:0, preferably 80:20 to 100:0, more preferably 90:10 to 100:0, and particularly preferably 95:5 to 100:0.

The obtained compound represented by General Formula (11) (general name of compounds represented by General Formulas (11a) and (11b)) is reacted, for example, in the presence of a solvent (for example, carbon tetrachloride), with a halogenating agent (for example, N-bromo succinimide (NBS), N-chloro succinimide (NCS), N-iodine succinimide (NIS), N,N-dibromo hydantoin (NDBH), N-bromo saccharin (NBSA), bromine, chlorine, or iodine) and a radical initiator (for example, 2,2'-azobis(iso butyronitrile)(AIBN)). Generally, the reaction is carried out by refluxing the mixture in a flask comprising a reflux condenser for a predetermined time. After the reaction, the reaction mixture is treated using a standard method, thereby obtaining the compound represented by General Formula (12) (general name of compounds represented by General Formulas (12a) and (12b)).

Thereafter, a base (for example, triethyl amine, diisopropylethylamine, pyridine, 4-dimethylaminopyridine, piperidine, DBU, $Na_2CO_3$, or NaOH) is acted on the compound represented by General Formula (12) in a solvent (for example, benzene, toluene, or xylene). Generally, a base is added to a solution of the compound represented by General Formula (12), and the mixture is refluxed for a predetermined time. After the reaction, the solvent is distilled off, followed by separation and purification through distillation, thereby obtaining the compound represented by General Formula (1) (general name of compounds represented by General Formulas (1a) and (1b)).

In the obtained compound represented by General Formula (1)(monomer), the enantiomeric ratio (i.e., a molar ratio of R-isomer to S-isomer) of the asymmetrical carbon (C*) to which $R^1$ and $R^2$ are bonded is the following: R-isomer (S-isomer):S-isomer (R-isomer)=70:30 to 100:0, preferably 80:20 to 100:0, more preferably 90:10 to 100:0, particularly preferably 95:5 to 100:0.

In particular, it is preferable to use the compound represented by General Formula (1c) as the monomer represented by General Formula (1) in view of the stereoregularity of the polymer resulting from radical polymerization. It is preferable to use isopropyl as $R^{11}$.

3. Usage

The polymer produced by the present invention contains a repeating unit having stereoregularity in the molecule. In particular, the polymer having the repeating unit represented by General Formula (3) is a polyfunctional polymer having a hydrophilic hydroxy group and a carboxyl group on the same carbon. The compound therefore has a particular property derived from this configuration.

For example, in contrast to an atactic structure or syndiotactic structure that tends to form lactone in the molecule, the polymer of the present invention, which has high isotactic regularity, has a characteristic of the free hydroxy group and carboxyl group being effectively present in the molecule, enabling efficient formation of chelate compounds with various metal ions.

Moreover, the present invention ensures significantly high hydrophilicity not only for the homopolymer of the monomer represented by General Formula (1), but also for a copolymer of the monomer represented by General Formula (1) and another monomer (comonomer). When the polymer comes in contact with water, the volume of the polymer increases by 50 to 3000 times. For a copolymer, the above characteristic is exhibited insofar as the amount of the monomer represented by General Formula (1) is about 10 to 100 mol %.

Furthermore, the polymers having repeating units represented by General Formulas (4), (6), and (8) have an idiosyncratic structure; therefore, they may be used as new functional materials.

Since the polymer having a repeating unit represented by General Formula (3) of the present invention has the aforementioned characteristic, it is useful for, for example, bleaching disinfection adjuvants, surfactants, polymer coagulants, chelating agents, polyelectrolytes, antistatic agents (for textiles, clothes, etc.), sanitary articles (high performance polymer absorbents, ice packs, etc.), defogging materials (defogger for glass), adhesives, biofunctional materials, medical and environmental conservation materials, surface modifiers (coating of metal surfaces of mobile phones or other electronic equipment), protective films, high-performance polarizing films for liquid crystal displays or the like, photoresist materials, optical fiber materials, ink materials, and light-absorptive materials for plasma display panels.

EXAMPLES

The present invention is more specifically explained below in reference to the Examples. The present invention is, however, not limited to those examples.

Measurement Instruments

In the Examples and Comparative Examples, property measurement was carried out using the following instruments.

$^1$H-NMR and $^{13}$C-NMR: JEOL EX-400 (400 MHz)

IR: JASCO FT/IR-230

Optical Rotation: JASCO P-1030

Separation, Purification: Tosoh HLC-8020

Molecular Weight (Number-Average Molecular Weight (Mn), Weight-Average Molecular Weight (Mw)) and Molecular Weight Distribution (Mw/Mn): GPC (gel permeation chromatography): Tosoh HLC-8220 (column: TSKgel G7000HHR+G5000HHR+G3000) polystyrene standard Monomer Production

Production Example 1

Synthesis of 5-methylene-2-isopropyl-1,3-dioxolan-4-one 43.6 g (0.60 mol) of isobutyl aldehyde, 62.5 g (0.55 mol) of L-lactic acid, and 1.06 g (0.05 mmol) of p-toluene sulfonic acid were dissolved in 50 ml of n-pentane, and the mixture was refluxed for 8 hours in a 500-ml flask attached to a reflux condenser comprising a Dean-Stark fractionator. After the reaction, the reaction mixture was neutralized and washed with a sodium bicarbonate aqueous solution, followed by extraction with ether. Thereafter, the extract was dried with anhydrous magnesium sulfate. Thereafter, ether was distilled off, thereby giving 62.7 g (yield=79.2%) of 5-methyl-2-isopropyl-1,3-dioxolan-4-one as a diastereomer mixture.

Next, column chromatography (developing solvent: hexane/ether=20/1) was carried out to obtain a mixture of cis-isomer/trans-isomer (steric structural relationship of methyl group and isopropyl) of 80/20, and only cis-isomers were separated by optical resolution.

5-methyl-2-isopropyl-1,3-dioxolan-4-one (cis-isomer)

IR (neat, cm$^{-1}$) 1802 (C=O), 2883-2974 (isopropyl)

$^1$H-NMR (CDCl$_3$, ppm) 1.01 (d, J=7.2 Hz, 6H), 1.49 (d, J=6.8 Hz, 3H), 2.00 (m, 1H), 4.35 (q, J=6.8 Hz, 1H), 5.28 (d, J=4.4 Hz, 1H) [α]$_D$=+25.7 (optical rotation at Nα-D line, [compound]=0.2 g/dl, in CHCl$_3$)

60.0 g (0.41 mol) of the cis-isomers of 5-methyl-2-isopropyl-1,3-dioxolan-4-one obtained above, 73.8 g (0.41 mol) of N-bromo succinimide, and 180 mg (1.1 mmol) of 2,2'-azobis(isobutyronitrile)(AIBN) were dissolved in 180 ml of carbon tetrachloride and refluxed for 4 hours in a flask comprising a reflux condenser. After the reaction, the precipitated salt was removed by filtration, and the carbon tetrachloride in the filtrate was distilled off, giving 83.0 g (0.36 mol) of 5-bromo-5-methyl-2-isopropyl-1,3-dioxolan-4-one.

The bromo isomer in 350 ml of dry benzene were placed in a flask comprising a dropping funnel and a reflux condenser, and 46.5 g (0.46 mol) of triethyl amine mixed with 150 ml of dry benzene was slowly added thereto dropwise over 1 hour in a nitrogen atmosphere with ice-cooling, followed by 1 hour of reflux. After the reaction, the precipitated salt was removed by filtration, and the dry benzene in the filtrate was distilled off. Thereafter, separation and purification were performed by distillation (bp=65° C./7 mmHg), thereby giving 20.0 g (yield=38.9%) of 5-methylene-2-isopropyl-1,3-dioxolan-4-one.

5-methylene-2-isopropyl-1,3-dioxolane-4-one

IR (neat, cm$^{-1}$) 1668 (C=C), 1798 (C=O), 2883-2974 (isopropyl)

$^1$H-NMR (CDCl$_3$, ppm) 1.00 (d, J=0.8 Hz, 3H), 1.02 (d, J=0.8 Hz, 3H), 2.04 (m, 1H), 4.86 (d, J=2.8 Hz, 1H), 5.15 (d, J=2.8 Hz, 1H), 5.60 (d, J=4.4 Hz, 1H)

[α]$_D$=−6.8 (CHCl$_3$)

Production Example 2

Synthesis of 5-methylene-2-isopropyl-1,3-dioxolan-4-one 5-methylene-2-isopropyl-1,3-dioxolan-4-one was synthesized by a different method from that of Production Example 1.

43.6 g (0.60 mol) of isobutyl aldehyde, 62.5 g (0.55 mol) of ferment lactic acid, and 1.06 g (0.05 mmol) of p-toluene sulfonic acid were dissolved in 50 ml of n-pentane, and the mixture was refluxed for 8 hours in a 500-ml flask attached to a reflux condenser comprising a Dean-Stark fractionator. After the reaction, the reaction mixture was neutralized and washed with a sodium bicarbonate aqueous solution, followed by extraction with ether. Thereafter, the ether solution was dried with anhydrous magnesium sulfate. Thereafter, ether was distilled off, and 65.3 g (yield=82.5%) of the target 5-methyl-2-isopropyl-1,3-dioxolan-4-one was obtained from the reaction mixture through distillation under reduced pressure. The target product was a diastereomer mixture wherein the ratio of cis-isomer/trans-isomer (see Production Example 1) was 80/20. The product was subjected to the next reaction without optical resolution. The following step was performed according to the monomer synthesis of Production Example 1.

The generation of the target product was confirmed using IR, 1H-NMR. The optical rotation of the obtained 5-methylene-2-isopropyl-1,3-dioxolan-4-one was [α]$_D$=−5.5 (CHCl$_3$).

Production Example 3

Synthesis of 5-methylene-2-isopropyl-1,3-dioxolan-4-one using racemate of lactic acid 43.6 g (0.60 mol) of isobutyl aldehyde, 62.5 g (0.55 mol) of a racemic mixture of D-lactic acid and L-lactic acid, and 1.06 g (0.05 mmol) of p-toluene sulfonic acid were dissolved in 50 ml of n-pentane, and the mixture was refluxed for 8 hours in a 500-ml flask attached to a reflux condenser comprising a Dean-Stark fractionator. The following step was performed according to the monomer synthesis of Production Example 2.

The generation of the target product was confirmed using IR, 1H-NMR. The optical rotation of the obtained 5-methylene-2-isopropyl-1,3-dioxolan-4-one was [α]$_D$=0 (CHCl$_3$).

Production Example 4

Synthesis of 5-methylene-2,2-pentamethylene-1,3-dioxolan-4-one

[Chem. 14]

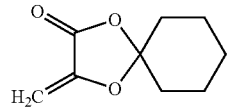

5.0 g (0.05 mol) of cyclohexanone, 6.9 g (0.05 mol) of β-chloro lactic acid, and 0.1 g (6.5 mmol) of p-toluene sulfonic acid were dissolved in 30 ml of toluene, and the mixture was refluxed for 8 hours in a 100-ml flask attached to a reflux condenser comprising a Dean-Stark fractionator. After the reaction, the reaction mixture was neutralized and washed with a sodium bicarbonate aqueous solution, followed by extraction with ether. Thereafter, the extract was dried with anhydrous magnesium sulfate. Thereafter, ether was distilled off, and the residue was subjected to distillation under reduced pressure (bp=84° C./1.5 mmHg), thereby obtaining 6.8 g (yield=65.6%) of 5-chloromethyl-2,2-pentamethylene-1,3-dioxolan-4-one.

5-chloromethyl-2,2-pentamethylene-1,3-dioxolan-4-one

IR (neat, cm−1) 1800 (C=O), 2880-2975 (isopropyl)

$^1$H-NMR (CDCl$_3$, ppm) 1.35-1.95 (m, 10H), 3.80 (d, J=7.0 Hz, 2H), 4.70 (t, J=7.0 Hz, 1H)

5-chloromethyl-2,2-pentamethylene-1,3-dioxolan-4-one 6.4 g (0.03 mol) thus obtained and 30 ml of toluene were placed in a flask comprising a dropping funnel and a reflux condenser, and 4.4 ml (0.03 mol) of diisopropylamine mixed with 10 ml of toluene was slowly added thereto dropwise with ice-cooling over 1 hour, followed by further reaction for 4 hours at 75° C. After the reaction, the precipitated salt was removed by filtration, and benzene in the filtrate was distilled off. Thereafter, separation and purification were performed by distillation (bp=62° C./1.5 mmHg), thereby giving 4.2 g (yield=79.6%) of 5-methylene-2,2-pentamethylene-1,3-dioxolan-4-one.

5-methylene-2,2-pentamethylene-1,3-dioxolan-4-one

IR (neat, cm$^{-1}$) 1668 (C=C), 1800 (C=O), 2880-2975 (isopropyl)

$^1$H-NMR (CDCl$_3$, ppm) 1.30-1.75 (m, 10H), 4.68 (d, J=2.8 Hz, 1H), 4.97 (d, J=2.8 Hz, 1H)

Radical Polymerization Reaction

Example 1

[Chem. 15]

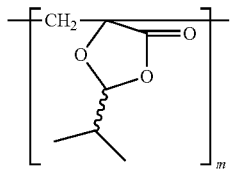

5 ml (0.026 mol) of the monomer (5-methylene-2-isopropyl-1,3-dioxolan-4-one) obtained in Production Example 1 and 8.2 mg (0.05 mmol) of AIBN were stirred for 2 hours in a nitrogen-substituted glove box. After the reaction, the solution was poured into a large amount of n-hexane (about 20 times the solution) under stirring. The precipitated polymer was subjected to suction filtration and drying at room temperature, thereby obtaining a target product (white solid). Table 1 shows the results.

Example 2 and Comparative Examples 1 and 2

Polymers were obtained in the same manner as in Example 1 except that the type of monomer and the reaction conditions were changed as shown in Table 1. Table 1 shows the results.

Because the solubility depends on the structure, the isotactic polymers (Examples 1 and 2) are insoluble in benzene, toluene, acetonitrile, etc., unlike the atactic polymer (Comparative Example 1).

Example 3

In a nitrogen-substituted glove box, 7 ml (52 mmol) of the monomer of Production Example 1, 3 ml (26 mmol) of styrene, and 16.4 mg (0.1 mmol) of AIBN were stirred for 10 hours at 60° C. After the reaction, the solution was poured into a large amount of n-hexane (about 20 times the solution) under stirring. The precipitated polymer was subjected to suction filtration and drying at room temperature, thereby obtaining a target product (white solid). Table 2 shows the results.

Example 4

In a nitrogen-substituted glove box, 9.5 ml (71 mmol) of the monomer of Production Example 1, 0.5 ml (3.5 mmol) of divinylbenzene, and 16.4 mg (0.1 mmol) of AIBN were polymerized for 25 hours at 60° C. After the polymerization, the polymer was separated and dried for 50 hours at 50° C. Table 2 shows the results.

Example 5

In this example, living radical polymerization of a monomer was carried out using ethyl-2-methyl-2-butyltellanyl-propionate.

1.34 ml (10 mmol) of the monomer (5-methylene-2-isopropyl-1,3-dioxolan-4-one) of Production Example 1, 12.9 mg (0.05 mmol) of ethyl-2-methyl-2-butyltellanyl-propionate, and 1.6 mg (0.01 mmol) of AIBN were dissolved in 1.3 ml of ethyl acetate and reacted for 15 hours at 60° C. After the reaction, the solution was dissolved in 5 ml of THF, and the resulting solution was poured into a large amount of n-hexane (about 20 times the solution) under stirring. The precipitated polymer was subjected to suction filtration and drying at room temperature, thereby obtaining a target product (white solid). Table 3 shows the results.

Example 6

In this example, living radical polymerization of a monomer was carried out using ethyl-2-methyl-2-butyltellanyl-propionate and di-n-butyl ditelluride The same method as in Example 5 was used except that equal quantities of ethyl-2-methyl-2-butyltellanyl-propionate and di-n-butyl ditelluride were used (0.05 mmol in total). Table 3 shows the results.

Example 7

In this example, living radical polymerization was carried out using ethyl 2-bromo isobutylate CuBr/CuBr2/N,N,N',N'',N''-pentamethyl diethylene triamine=8.6 mg (0.06 mmol)/0.7 mg (0.003 mmol)/12.1 mg (0.07 mmol) with respect to 1.34 ml (10 mmol) of monomer (5-methylene-2-isopropyl-1,3-dioxolan-4-one) of Production Example 1 were dissolved in 1.66 ml of anisole in a nitrogen-substituted glove box. Then, 11.7 mg (0.06 mmol) of ethyl 2-bromo isobutylate as an initiator was added thereto, and the mixture was stirred for 30 minutes at room temperature. Thereafter, the mixture was further reacted for another hour at 70° C. After the reaction, and the resulting solution was poured into a large amount of n-hexane (about 20 times the solution) under stirring. The precipitated polymer was subjected to suction filtration and drying at room temperature, thereby obtaining a target product (white solid). Table 3 shows the results.

Ring-Opening Reaction (Hydrolysis)

Example 8

Hydrolysis

[Chem. 16]

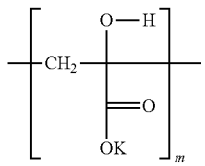

1.00 g of the polymer obtained in Example 1 and 300 ml of THF were placed in a flask, and the mixture was stirred until the polymer was dissolved or swollen. 5 g of KOH was added thereto and the mixture was reacted for 24 hours at room temperature. After the reaction, THF was distilled off using an evaporator, and methanol was added to the residue to precipitate a polymer. Thereafter, the precipitated polymer was subjected to suction filtration and drying at room temperature. Then, the polymer was purified using a dialysis membrane (Spectra/por 7, Spectrum Co. USA, molecular weight cut off value=3,500). The obtained amount of the purified hydrolyzed polymer was 0.812 g (yield=91.5%).

It was confirmed using IR that the obtained polymer was hydrolyzed polymer.

IR (KBr, cm−1) 1620 (br, C=O), 3450 (br, OH)

FIG. 1 and Table 1 show the measurement results of stereoregularity (tacticity) of the main chain quaternary carbon region of the polymer, with the results measured using $^{13}$C-NMR. The determination of stereoregularity using $^{13}$C-NMR was performed according to the following document: Yamazawa, K.: Kawauchi, S.; Sato, M. J., Polym. Sci. Part B: Polym. Phys. 2002, 40, 1400.

Example 9 and Comparative Examples 3 and 4

Polymers were obtained in the same manner as in Example 8 except that the type of monomer was changed as shown in Table 1. FIG. 1 and Table 1 show the measurement results of stereoregularities (tacticities) of the main chain quaternary carbon regions of the obtained polymers, with the results measured using $^{13}$C-NMR. The values represented by m and r were found from the absorption intensity of $^{13}$C-NMR, according to the following equations: m=mm+(mr/2) and r=rr+(mr/2).

As is evident from the comparison between Examples 8 and 9, and Comparative Examples 3 and 4 in Table 1, a polymerization system using a chiral monomer produces stereoregular (isotactic) polymer.

Figure 3:
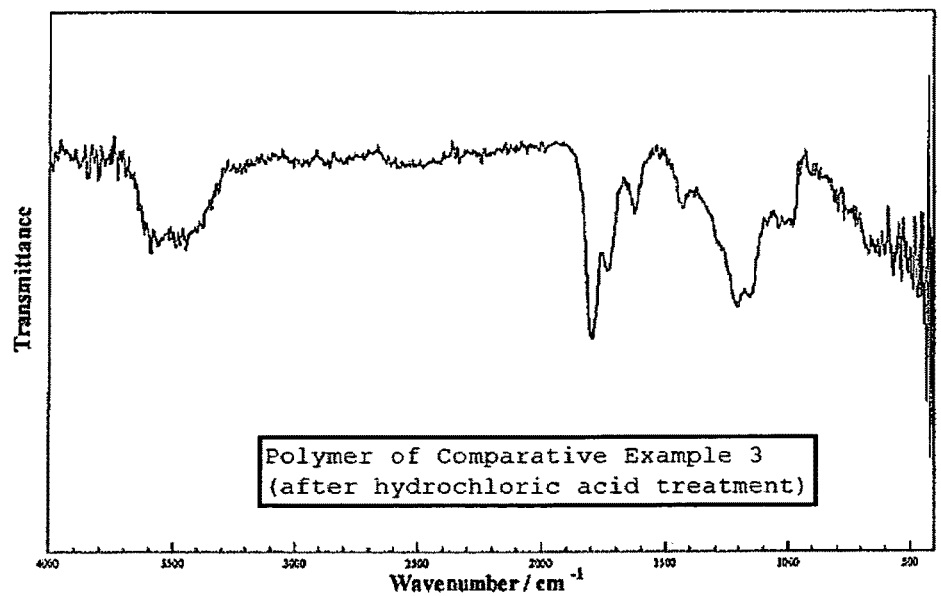
FIG. 3 shows IR charts of polymers obtained by treating polymers produced in Comparative Example 3 and Example 9 with 1N hydrochloride (HCl).
Figure 3:
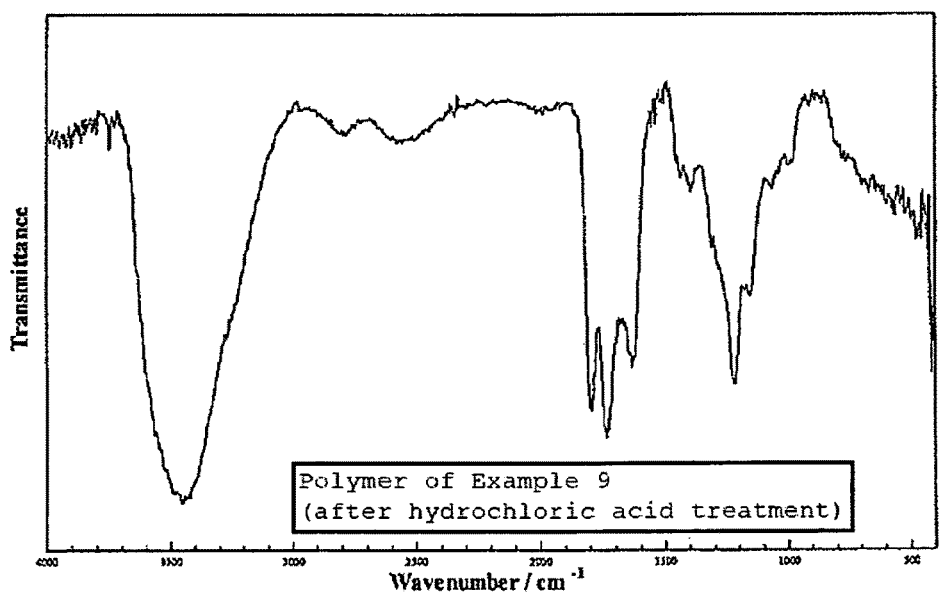

FIG. 3 shows IR of the polymers obtained by treating the polymers of Comparative Example 3 and Example 9 with 1N hydrochloric acid. IR of Comparative Example 3 shows intensive absorption of 1790 cm$^{-1}$, which indicates generation of a lactone ring. In contrast, in IR of Example 9, absorption of 1720 cm$^{-1}$, which indicates generation of carboxylic acid, is even more intensive than the lactone ring. This revealed that the isotactic polymer obtained in this research ensures effective functions of a carbonyl group and hydroxy group in an acidic solution. This advantage is not obtained by an atactic or syndiotactic polymer in which a COOK group and an OH group are adjacently positioned (Miyagawa, T.; Sanda, F.; Endo, T. J., Polym. Sci. Part A: Polym. Chem. 2001, 39, 1629).

Example 10

A hydrolyzed polymer was produced in the same manner as in Example 8 using the polymer obtained in Example 3. The stereoregularity (tacticity) was measured using $^{13}$C-NMR only with respect to the monomer chain in the copolymer. Table 2 shows the results.

Example 11

Figure 2:
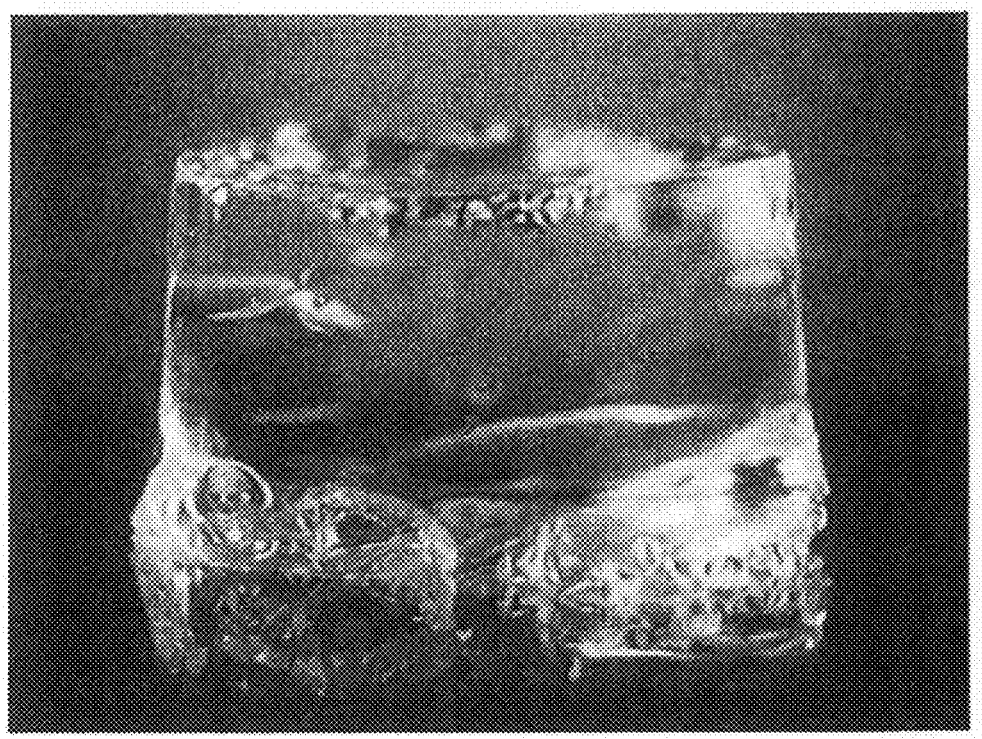
FIG. 2 is a photo of a hydrogel obtained by swelling a polymer obtained in Example 11 with water (distilled water).

The polymer of Example 0.4 in the swollen state was hydrolyzed in THF in the same manner as in Example 8 using KOH. Thereafter, the polymer was subjected to suction filtration at room temperature, washed with water, and dried. Table 2 shows the results. FIG. 2 shows a photo of the hydrated gel obtained by swelling the produced polymer with water (distilled water). The polymer easily absorbed water and was swollen to a size of 1600 times. This is clearly shown in FIG. 2.

Examples 12 to 14

A hydrolyzed polymer was produced in the same manner as in Example 8 using the polymer obtained in Example 3. The stereoregularity (tacticity) was measured using $^{13}$C-NMR. Table 3 shows the results.

Example 15

Amidation Reaction

[Chem. 17]

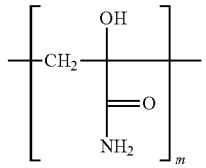

10 ml of concentrated ammonia water (SG=0.88) and 10 ml of water were placed in a flask, and 1.00 g of the polymer produced in Example 1 and 50 ml of THF were added thereto. The flask was sealed with a stopper and the mixture was stirred. During stirring, the stopper was removed from time to time to eliminate increased pressure inside the flask. After conducting this reaction for 30 minutes at room temperature, the reaction solution was concentrated, and n-hexane was added to the residue to precipitate a polymer. Thereafter, the precipitated polymer was subjected to suction filtration and dried at room temperature. The obtained amount of the polymer was 1.05 g (yield=92.7%).

Figure 4:
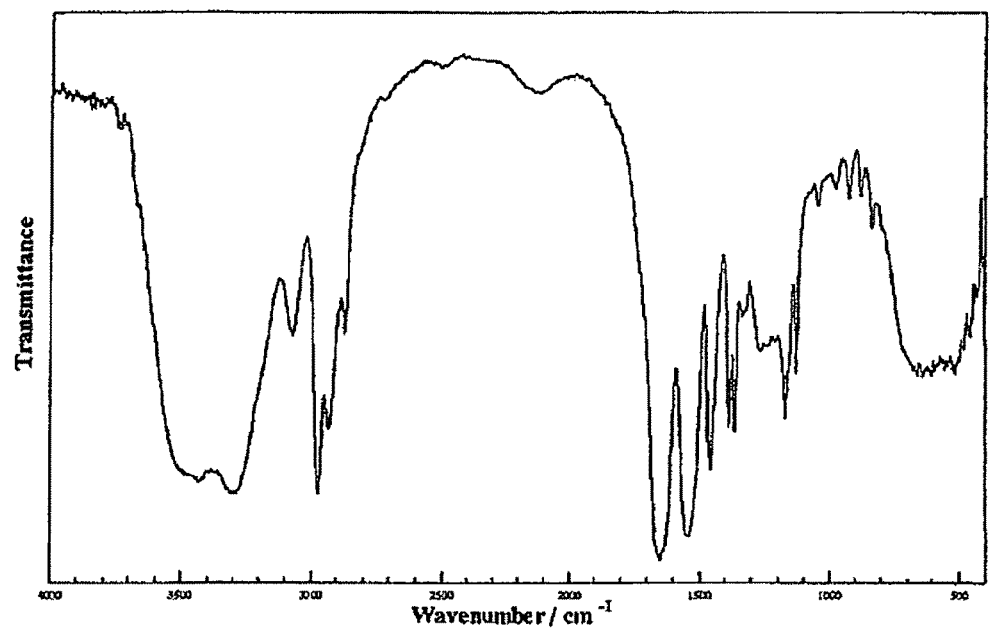
FIG. 4 shows an IR chart of a polymer obtained in Example 15.

IR confirmed that the obtained polymer was the target product (FIG. 4).

IR (KBr, cm$^{-1}$) 1655 (s, C=O), 3310 (br, NH), 3470 (br, OH)

Example 16

Ring-Opening Reaction

[Chem. 18]

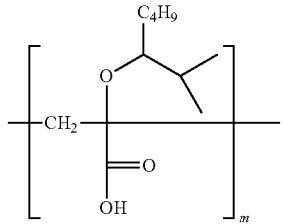

8.5 ml of ether solution containing 1.4 g of n-$C_4H_9MgBr$ was added to 14 mg of CuCl suspended in 20 ml of THF at 0° C. A chloroform solution of 1.00 g of the polymer obtained in Example 1 was added thereto dropwise, and the mixture was stirred for 20 minutes. Then, 3N hydrochloric acid was added and the liquid was separated. 3N sodium hydrate aqueous solution was added to the obtained organic layer to extract a polymer. Thereafter, the alcalic extract was acidified with hydrochloric acid, thereby precipitating the target polymer. The obtained amount of the polymer was 1.27 g (yield=91.1%).

Figure 5:
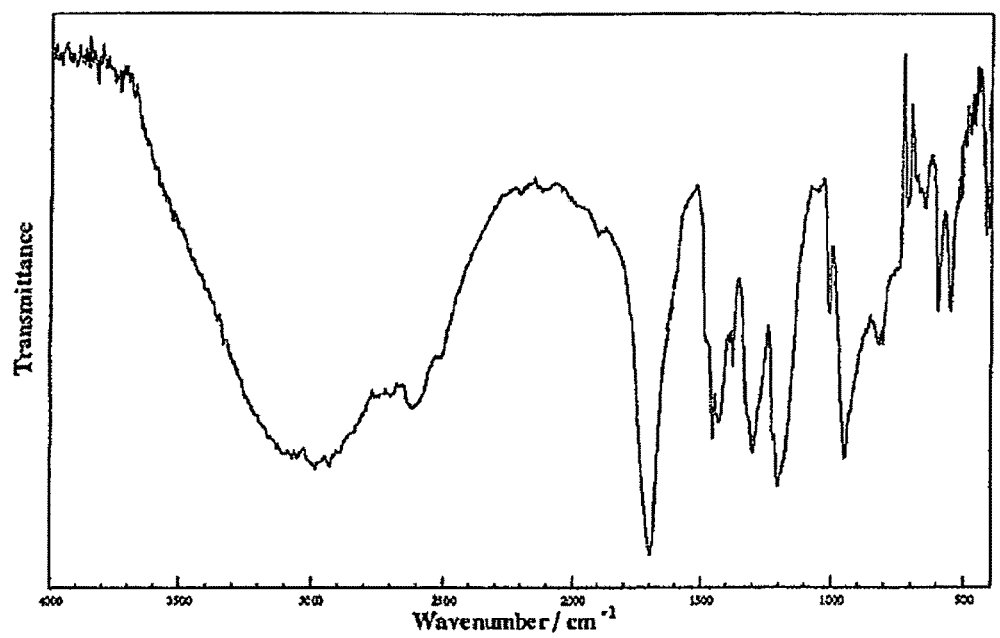
FIG. 5 shows an IR chart of a polymer obtained in Example 16.

IR confirmed that the obtained polymer was the target product (FIG. 5).

IR (KBr, $cm^{-1}$) 1705 (s, C=O), 3100 (br, OH)

Example 17

Reduction Reaction

[Chem. 19]

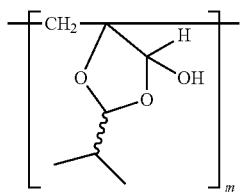

1.35 g of $LiAlH_4$ was dissolved in 10 ml of dry THF, and 5 ml of dry ethanol was added thereto at 0° C. to make a slurry of $LiAlH(OC_2H_5)_3$. Then, 10 ml of the slurry was added to 1.00 g of polymer obtained in Example 1 with ice-cooling and stirred for 2 hours. Thereafter, n-hexane was added to the reaction mixture to precipitate a polymer. Thereafter, the precipitated polymer was subjected to suction filtration and dried at room temperature. The obtained amount of the polymer was 0.897 g (yield=89.6%).

Figure 6:
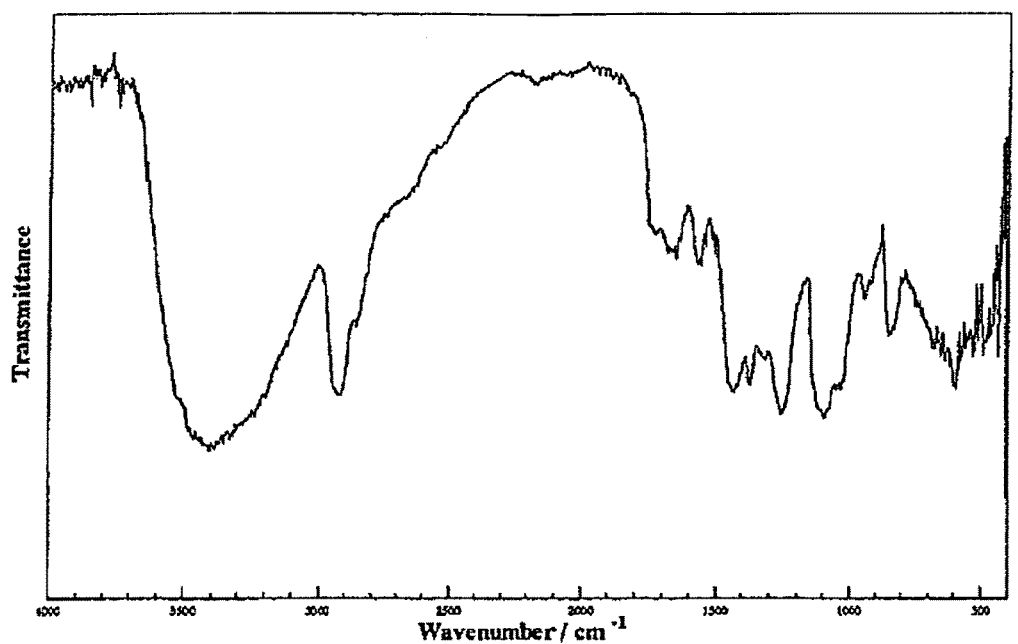
FIG. 6 shows an IR chart of a polymer obtained in Example 17.

IR showed that the absorption (1798 $cm^{-1}$) of the carbonyl group on the lactone ring disappeared, confirming that the obtained polymer was the target product (FIG. 6).

IR (KBr, $cm^{-1}$) 3450 (br, OH)

TABLE 1

| | | Polymerization Reaction | | | | | Hydrolysis of Polymer | |
|---|---|---|---|---|---|---|---|---|
| | Monomer | Temperature (° C.) | Time (h) | Yield (%) | Molecular weight (mn) | Mw/Mn | | Tacticity |
| Example 1 | Production Example 1 | 60 | 2 | 96.2 | — | — | Example 8 | m:r = 100:0 |
| Example 2 | Production Example 2 | 60 | 3 | 94.8 | 22,800 | 1.8 | Example 9 | m:r = 82:18 |
| Comparative Example 1 | Production Example 3 | 60 | 3 | 52.5 | 14,500 | 1.7 | Comparative Example 3 | m:r = 55:45 |
| Comparative Example 2 | Production Example 4 | 60 | 10 | 77.6 | 210,000 | 2.2 | Comparative Example 4 | m:r = 34:64 |

TABLE 2

| | Polymerization Reaction | | | | Hydrolysis of Polymer | |
|---|---|---|---|---|---|---|
| | Yield (%) | Styrene unit content in copolymer (mol %) | Molecular weight (mn) | Mw/Mn | | Tacticity |
| Example 3 | 38.5 | 11.2 | 217,000 | 2.3 | Example 10 | m:r = 71:29 |
| Example 4 | >97.0 | — | — | — | Example 11 | — |

TABLE 3

| | Polymerization Reaction | | | | | Hydrolysis of Polymer | |
|---|---|---|---|---|---|---|---|
| | Temperature (° C.) | Time (h) | Yield (%) | Molecular weight (mn) | Mw/Mn | | Tacticity |
| Example 5 | 60 | 15 | 82.7 | 20,300 | 1.20 | Example 12 | m:r = 91:9 |
| Example 6 | 60 | 15 | 85.2 | 20,800 | 1.23 | Example 13 | m:r = 88:12 |
| Example 7 | 70 | 1 | 88.5 | 14,100 | 1.18 | Example 14 | m:r = 90:10 |

The invention claimed is:

1. A polymer having, in a molecule, a repeating unit represented by Formula (2):

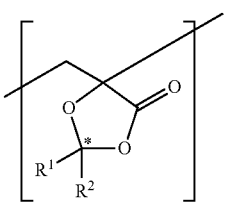

(2)

wherein $R^1$ and $R^2$ are different, and each represents a hydrogen atom, a linear or branched C1-10 alkyl group, aryl group, or heteroaryl group; and * represents an asymmetrical carbon, the polymer containing meso diad (m) and racemo diad (r) at a proportion of 60:40 to 100:0 (m:r).

2. A process for producing the polymer according to claim 1, comprising subjecting a monomer containing a compound represented by Formula (1) to radical polymerization,

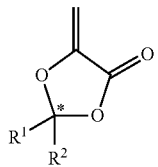
(1)

wherein $R^1$, $R^2$ and * are the same as above,
the compound having R-isomers and S-isomers at a ratio of: R-isomer (S-isomer):S-isomer (R-isomer)=70:30 to 100:0.

3. A process for producing a polymer having, in a molecule, a repeating unit represented by Formula (3):

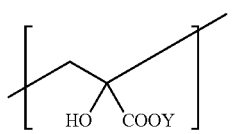
(3)

wherein, Y represents a hydrogen atom or countercation,
the polymer containing meso diad (m) and racemo diad (r) at a proportion of 60:40 to 100:0 (m:r),
the process comprising subjecting a monomer containing a compound represented by Formula (1) to radical polymerization to obtain the polymer according to claim 1; and hydrolyzing the polymer,

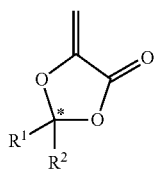
(1)

wherein $R^1$ and $R^2$ are different, and each represents a hydrogen atom, a linear or branched C1-10 alkyl group, aryl group, or heteroaryl group; and * represents an asymmetrical carbon,
the compound having R-isomers and S-isomers at a ratio of: R-isomer (S-isomer):S-isomer (R-isomer)=70:30 to 100:0.

4. A process for producing a polymer having, in a molecule, a repeating unit represented by Formula (3):

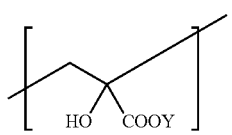
(3)

wherein, Y represents a hydrogen atom or countercation,
the polymer containing meso diad (m) and racemo diad (r) at a proportion of 60:40 to 100:0 (m:r),
the process comprising hydrolyzing the polymer according to claim 1.

5. A process for producing a polymer having, in a molecule, a repeating unit represented by Formula (4):

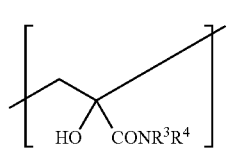
(4)

wherein, $R^3$ and $R^4$ are the same or different, and each represents a hydrogen atom, an alkyl group that may or may not be substituted, an aryl group that may or may not be substituted, or a heteroaryl group that may or may not be substituted; or $R^3$ and $R^4$ may be bonded to each other to form a ring together with an adjacent nitrogen (N),
the polymer containing meso diad (m) and racemo diad (r) at a proportion of 60:40 to 100:0 (m:r),
the process comprising reacting the polymer according to claim 1 with a compound represented by Formula (5):

$HNR^3R^4$ (5)

wherein $R^3$ and $R^4$ are the same as above.

6. A process for producing a polymer having, in a molecule, a repeating unit represented by Formula (6):

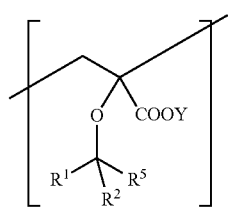
(6)

wherein $R^1$ and $R^2$ are different, and each represents a hydrogen atom, a linear or branched C1-10 alkyl group, aryl group, or heteroaryl group; $R^5$ represents an alkyl group that may or may not be substituted, an aryl group that may or may not be substituted, or a heteroaryl group that may or may not be substituted, and Y represents a hydrogen atom or countercation,
the polymer containing meso diad (m) and racemo diad (r) at a proportion of 60:40 to 100:0 (m:r),
the process comprising reacting the polymer according to claim 1 with a compound represented by Formula (7):

$R^5$-M (7)

wherein M represents a metal atom, and $R^5$ is the same as above.

7. A process for producing a polymer having, in a molecule, a repeating unit represented by Formula (8):

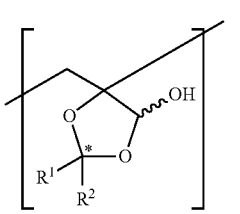

wherein $R^1$ and $R^2$ are different, and each represents a hydrogen atom, a linear or branched C1-10 alkyl group, aryl group, or heteroaryl group; * represents an asymmetrical carbon, the polymer containing meso diad (m) and racemo diad (r) at a proportion of 60:40 to 100:0 (m:r), the process comprising reducing the polymer according to claim 1 by contacting with a reduction reagent.

* * * * *